United States Patent [19]

Pitesky

[11] 4,008,718
[45] Feb. 22, 1977

[54] LIQUID FILTERING AND DISPENSING ASSEMBLY

[76] Inventor: Isadore Pitesky, 4001 Linden Ave., Long Beach, Calif. 90807

[22] Filed: Feb. 26, 1976

[21] Appl. No.: 661,835

[52] U.S. Cl. .......................... 128/218 R; 128/234; 128/272.3; 222/189; 92/78
[51] Int. Cl.² ......................................... A61M 5/00
[58] Field of Search .......... 128/234, 218 R, 218 P, 128/218 PA, 218 C, 218 M, 215, 220, 221, 272.1, 272.3; 222/189, 386, 387, 309; 92/78

[56] References Cited
UNITED STATES PATENTS

| | | | |
|---|---|---|---|
| 3,366,286 | 1/1968 | Kloehn | 222/386 |
| 3,417,904 | 12/1968 | McLay | 128/218 C X |
| 3,677,448 | 7/1972 | Harris, Sr. et al. | 128/218 C |
| 3,746,216 | 7/1973 | Frederick | 128/218 M X |
| 3,921,864 | 11/1975 | Dawes | 222/386 |

Primary Examiner—John D. Yasko
Attorney, Agent, or Firm—William C. Babcock

[57] ABSTRACT

An elongate, portable, hand-operated assembly adapted to create either a negative or positive pressure within the interior thereof, with the device being capable of having a hypodermic needle removably mounted on either end thereof. The assembly may be actuated to create a negative pressure to draw a liquid that may contain entrained particles of solid material into the interior of the assembly. After the assembly has introduced liquid therein in a desired volume, it may subject the liquid to positive pressure to separate particles of solid material such as protein, bacteria and viruses from the liquid.

Liquid free of solid particles, may be discharged from the assembly through a hypodermic needle that is removably secured to the assembly. A magnetically attractable body may rest on the filter within the interior of the assembly. When that body is subjected to a rotating magnetic field, the body moves concurrently with the field, and in so moving, the body removes caked, solid particles from the filter to facilitate the flow of liquid through the latter.

10 Claims, 9 Drawing Figures

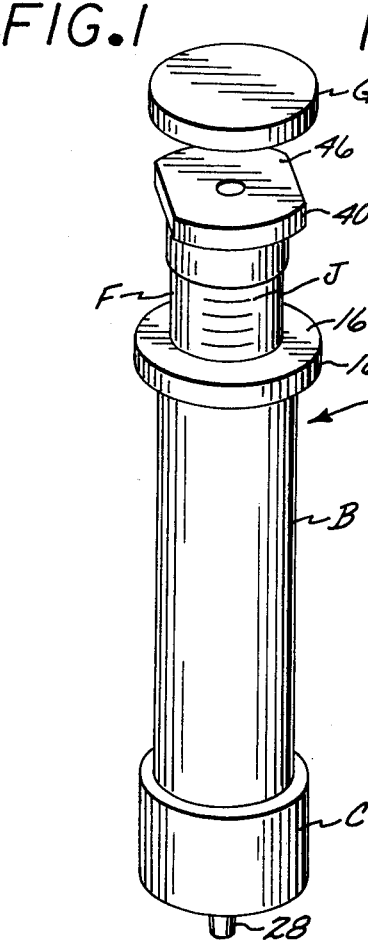
FIG.1
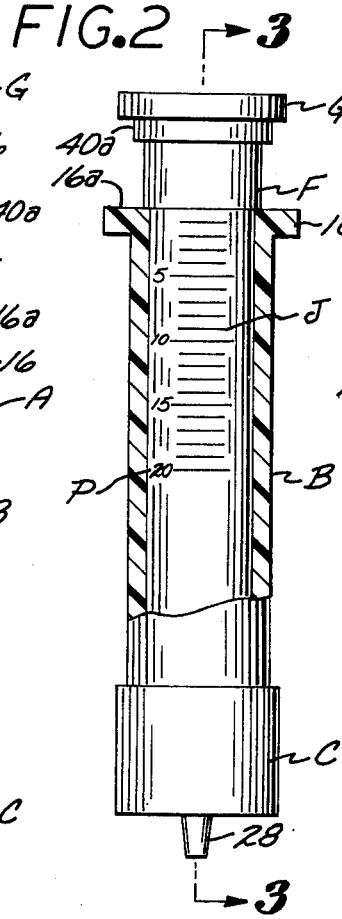
FIG.2
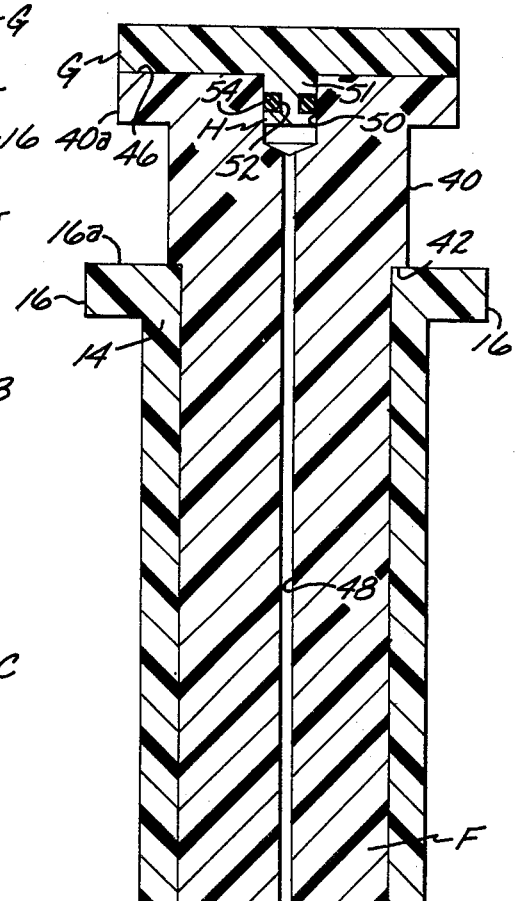
FIG.3
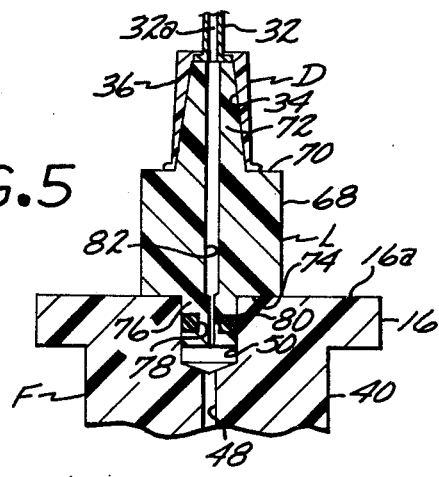
FIG.5
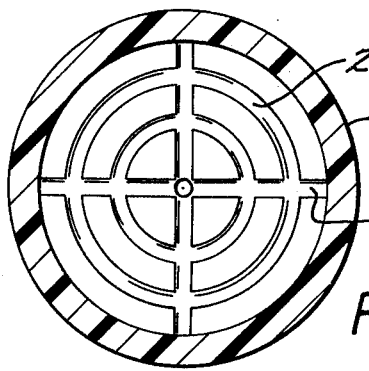
FIG.4
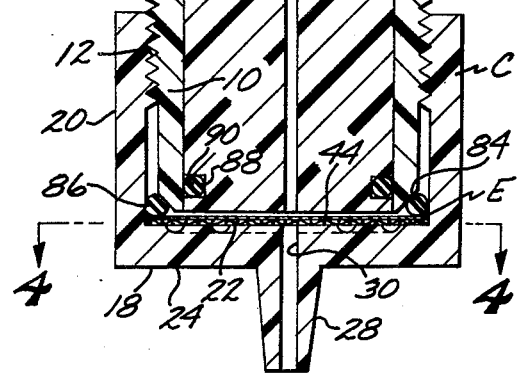

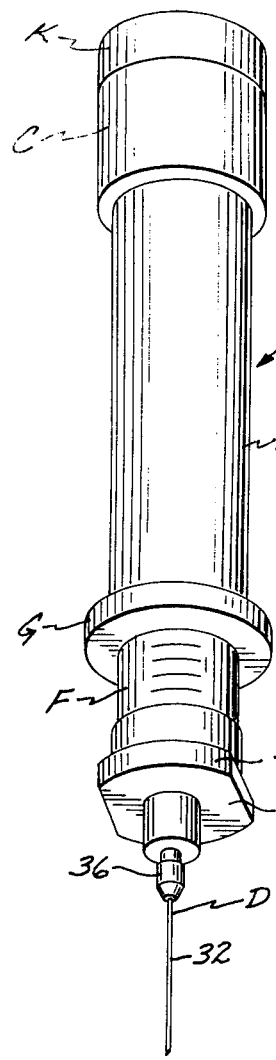
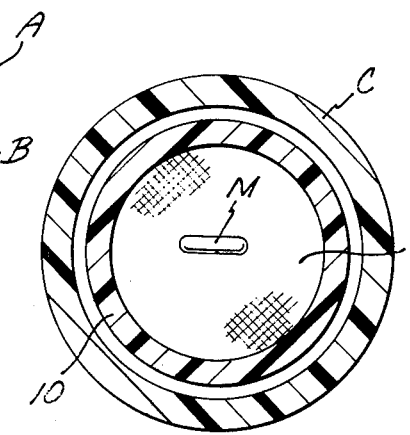
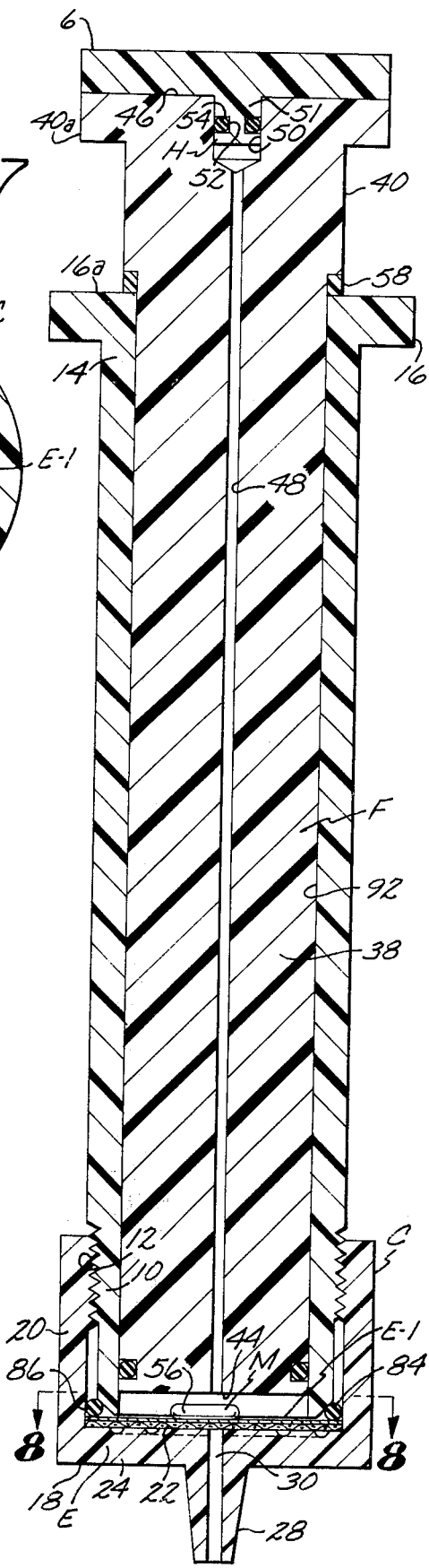
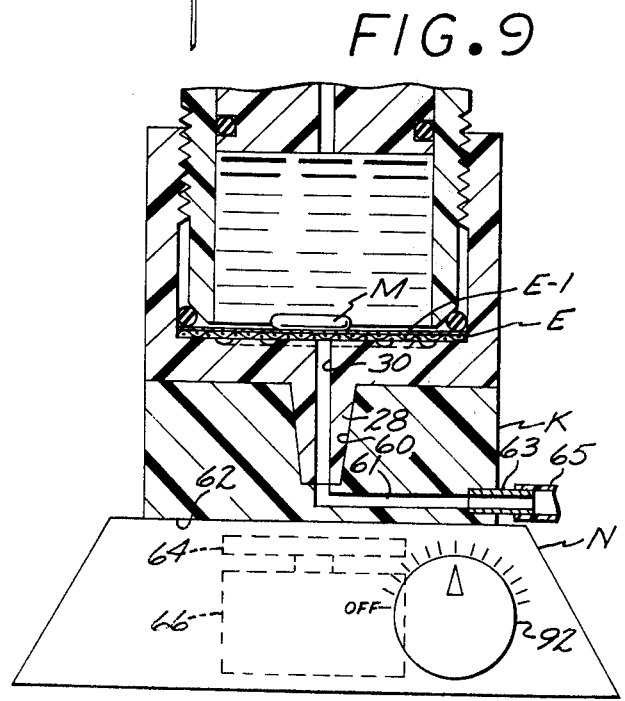

1

LIQUID FILTERING AND DISPENSING ASSEMBLY

BACKGROUND OF THE INVENTION

1. Field of the Invention

Liquid filtering and dispensing assembly.

2. Description of the Prior Art

In many fields of scientific endeavor, particularly in medicine, it is desirable to subject a relatively small quantity of liquid to pressure whereby particled solid materials, bacteria or viruses may be removed from the liquid. Prior to the present invention, there has been no lightweight, portable, hand-operated device or assembly that permits the handling of a liquid under sterile conditions to accomplish the above-mentioned objectives in an easy and convenient manner.

A major object of the present invention is to provide an assembly, which in conjunction with a conventional hypodermic needle, may be used to withdraw a quantity of liquid into a confined space under a negative pressure, and thereafter subject said liquid to a positive pressure to remove particled solid materials therefrom by filtering prior to discharge of the liquid from the assembly.

Another object of the invention is to furnish an assembly in which caked, solid material may be separated from the filter forming a part thereof by magnetically actuated means without dismantling the assembly, and during the filtering operation, which is particularly useful when the solid material is protein.

SUMMARY OF THE INVENTION

The invention is a portable hand-operated assembly capable of being manipulated by a user to contain a quantity of a liquid, and thereafter filter the liquid to remove particles of solid material therefrom. After the liquid is free of solid particles, a desired metered quantity of the liquid may be discharged into a desired container, or through a hypodermic needle, which needle includes a head in which a tapered recess is defined.

In detail, the assembly includes an elongate cylindrical barrel that has a first end portion on which external threads are defined and a second end portion which includes an outwardly extending flange that may be engaged by the forefinger and middle finger of a user's hand.

A cup is provided that includes a circular web, which cup has an internally threaded side wall extending from the periphery thereof, with the web including first and second oppositely disposed sides, and the first side having a number of spaced grooves defined therein. The cup includes a tapered first protuberance that extends outwardly from the second side of the web, with the first protuberance having a longitudinal first bore formed therein that is in communication with the grooves. The first protuberance is adapted to removably and sealingly engage a tapered recess in a hypodermic needle head to support the hypodermic needle from the cup.

The cup is secured to the barrel by engagement of the internally threaded side wall thereof with the external threads on the barrel to removably support the cup in a fixed position relative to the barrel.

A flat circular screen rests on the first side of the web, and is of such diameter as to extend under the first end portion of the barrel and the screen supporting a flat filter membrane. The screen cooperates with the grooves on the first ends of the web to define a number of spaced passages through which filtered liquid may flow to the first longitudinal bore. A first resilient sealing ring is disposed in the cup and is deformed by pressure contact with the extremity of the first end portion of the barrel to seal with an outer peripheral portion of the filter membrane. An elongate ram having first and second axially aligned portions is provided, which portions at their junction define a circular body shoulder. The first end portion snugly and slidably engages the interior surface of the barrel. The first portion has a first free end surface and the second portion a second free end surface. A longitudinal second bore is formed in the ram that extends between the first free end surface thereof and a cavity that extends inwardly into the ram from the second free end surface. The body shoulder acts as a stop when it engages the outer extremity of the second portion of the barrel to prevent the first free end surface of the ram pressure contacting the filter member as the ram is moved inwardly in the barrel.

The first portion of the ram has a circumferential groove therein adjacent the first free end surface thereof. A second resilient sealing ring is mounted in the groove and is slidable sealing contact with the interior surface of the barrel, with the second longitudinal bore and cavity allowing an air bubble in the barrel to escape to the ambient atmosphere when the ram is moved towards the cap. The expulsion of all air from the barrel of the assembly is signaled when liquid from the barrel starts to discharge into the cavity.

A plate is provided that overlies the second free end surface of the ram, and the plate having first means that project therefrom and removably engage the cavity and seal with the latter. The plate is positional on the ram after all air above the liquid in the barrel has been discharged from the barrel. The plate is capable of being engaged by the thumb of the hand of a user as the fore-finger and middle finger of the hand engage the flange on the second end portion of the barrel. The first free end of the ram may now be moved towards the cup to force liquid in the barrel through the filter membrane to discharge into the first longitudinal passage to flow therefrom into a desired container or through a hypodermic needle that is removably secured to the first protuberance.

BRIEF DESCRIPTION OF THE DRAWING

FIG. 1 is a perspective view of the assembly;

FIG. 2 is a combined side elevational and longitudinal cross-sectional view of the assembly shown in FIG. 1;

FIG. 3 is a longitudinal cross-sectional view shown in FIG. 2 taken on the line 3—3 thereof of the assembly;

FIG. 4 is a transverse cross-sectional view of the assembly taken on the line 4—4 of FIG. 3;

FIG. 5 is a longitudinal cross sectional view of the upper portion of the ram with an adapter mounted thereon of which a hypodermic needle may be mounted;

FIG. 6 is a perspective view of the assembly, with a hypodermic needle removably secured thereto in such a matter that the hypodermic needle may puncture a pliable stopper in a container in which a liquid is disposed to withdraw a desired quantity of liquid into the interior of the assembly when the ram is moved outwardly relative to the barrel;

FIG. 6 is a perspective view of the assembly, with a hypodermic needle removably secured thereto in such a manner that the hypodermic needle may puncture a pliable stopper in a container in which a liquid is disposed, to withdraw a desired quantity of the liquid into the interior of the assembly when the ram is moved outwardly relative to the barrel;

FIG. 7 is a longitudinal cross-sectional view of the assembly with a magnetically attractable body supported on an upper surface of the filter member, and a spacing ring removably secured to the ram adjacent the body shoulder to act as a stop to limit the downward movement of the ram to the extent that the ram cannot contact the magnetically attractable body and force the latter into destructive pressure contact with the filter member;

FIG. 8 is a transverse cross-sectional view of the assembly on the line 8—8 of FIG. 7; and FIG. 9 is a fragmentary longitudinal cross-sectional view of the assembly resting on the upper surface of a table in which a magnet shown in phantom line is rotated to create a magnetic field, with the magnetically attractable body being moved over the filter member as a result of this magnetic field to remove caked solid particles from the filter member.

DESCRIPTION OF THE PREFERRED EMBODIMENT

The invention A, as may best be seen in FIGS. 1, 2 and 3, includes a cylindrical barrel B that has a cup C removably secured to a first end thereof. The barrel B, as best seen in FIG. 3, includes a first end portion 10 having external threads 12 defined thereon. The second end portion 14 of barrel B is provided with a flange 16 projecting outwardly therefrom.

Cup C includes a circular web 18 that has a cylindrical side wall 20 extending upwardly from the periphery thereof. The web also has a first side 22 and second side 24. Circumferentially and radially spaced grooves 26 are formed in the first side 22 of web 18, as may best be seen in FIG. 4. A first protuberance 28 of tapered configuration projects outwardly from the second side 24 of web 18, which protuberance has a longitudinal first bore 30 formed therein.

The hypodermic needle D shown in FIGS. 5 and 6 includes an elongate shank 32 in which a longitudinal bore 32a extends therethrough, with the bore being in communication with a tapered recess 34 formed in a head 36 secured to the shank. The recess 34 is of such tapered configuration that it may be removably wedged onto the first protuberance 28 to support the hypodermic needle O therefrom.

Ram F is best shown in FIG. 3, and includes first and second longitudinally aligned portions 38 and 40, which at their junction, define a transverse body shoulder 42. The first portion 38 of ram F has a first free end surface 44, as best seen in FIG. 3, and the second end portion 40 of ram F has a second free end surface 46. A second longitudinal bore 48 is defined in ram F and extends between the first free end surface 44 thereof and a cavity 50 that extends inwardly into the ram from the second free end surface 46 thereof. A plate G is provided that has a second protuberance 51 projecting therefrom in which a circumferential groove 52 is formed, with the groove serving to support a resilient sealing ring 54. When the pressure plate G is in the position shown in FIG. 3, the second protuberance 51 is disposed in cavity 50 to seal the latter.

A magnetically attractable body M shown in FIG. 7 is provided, that has an envelope 56 of an inert material such as a polymerized resin extending therearound. When the magnetically attractable body M is disposed within the assembly A and rests on the filter member E (FIG. 7), a spacing ring 58 is removably mounted on the first portion 38 of the ram F adjacent the body shoulder 42, with this spacing ring preventing the first free end surface 44 of the ram from moving downwardly to the extent it can contact the magnetically attractable body M and force the latter into pressure contact with the upper surface of the filter member E.

A body K is provided that is illustrated as being cylindrical body K has a tapered recess 60 extending downwardly from the upper surface of the body, as shown in FIG. 9 that may removably engage the first protuberance 28 to seal the first bore 30 formed in the latter. When the body K is mounted on the assembly A, as shown in FIG. 9, the lower surface 62 of body K may rest on the upper surface of the table N, which table has a rotatable magnet 64 situated within the confines thereof that is driven by an electric motor 66 to create a rotating magnetic field. As the magnetic field rotates in a horizontal plane, the magnetically attractable body M moves therewith, and in so doing removes solid particles (not shown) particularly proteins that have accumulated as a cake on the upper surface of a filter membrane E-1 that rests on the screen E, which cake if not removed, seriously impedes the flow of liquid from the interior of the assembly A to the first bore 30.

The adapter L, as may best be seen in FIG. 5, includes a central body 68 that has a first end 70 from which a first tapered membrane 72 extends. The body 64 includes a second end 74 from which a second member 76 extends that is of cylindrical configuration. A circumferential groove 78 is formed in the second member 76, and a resilient sealing 80 is disposed in this groove. A bore 82 extends longitudinally through the second member 76, body 64, and the first member 72, as shown in FIG. 5. When the plate G is removed from the second end portion of the ram F, the second member 72 may be inserted into the cavity 50, with the resilient ring 80 effecting a fluid seal therewith.

The graduations J preferably have numbers P associated therewith, which graduations and numbers cooperatively visually indicate the quantity of liquid in the assembly A, when one of the graduations is transversely aligned with the upper horizontal surface 16a of the flange 16. The free end of the second portion 40 of the ram F develops into a flange 40a on which the second free end surface 46 is defined, as shown in FIGS. 1 and 3.

The filter membrane E-1 is of conventional design and rests on the screen E that is mounted on the first side 22 of the web 18 to cooperate with the grooves 26 to provide a number of passages that are in communication with the first bore 30. The first portion 38 of ram F terminates in a ring-shaped tapered surface 78, as best seen in FIG. 3 that is in pressure contact with a resilient sealing ring 86 that rests on the upper peripheral portions of the filter membrane E-1.

When the cup C is screwed onto the threads 12 of barrel B, the tapered surface 84 is brought into pressure contact with the resilient sealing ring 86 to force the latter downwardly on the filter membrane E-1 and prevent the liquid in the invention A from bypassing the filter membrane E-1 to flow into the first bore 30 without being filtered. A circumferential groove 88 is defined in the lower portion of ram F, in which groove a resilient sealing ring 90 is disposed that is at all times in sealing engagement with the longitudinal interior surface 92 of the barrel B.

The invention A is used by removing the plate G from the ram F and inserting the second cylindrical member 76 of adaptor L into the cavity 50, as shown in FIG. 5. The hypodermic needle D is then mounted on first member 72, also as shown in FIG. 5. The needle D may thereafter be extended through a resilient stopper (not shown) in a bottle containing a sterile liquid. When the barrel B is moved longitudinally relative to the ram F away from the stop 42, a negative pressure is generated within the interior of the invention A and liquid is drawn through the hypodermic needle D, bore 82, and bore 48 into the interior of the invention. The graduations J indicate visually to a user (not shown) the quantity of liquid that has been drawn into the invention A by the steps above described. After a desired quantity of liquid has been drawn into the invention A, the needle D is withdrawn from the stopper, and the user, while holding the invention A is an upright position, presses downwardly on the ram F. The barrel B may also have liquid poured therein and the ram F then inserted into the barrel when the latter procedure is used there will be a bubble of air between the bottom of the ram and upper surface of the liquid in the barrel. This downwardly directed force when the last mentioned procedure is used moves the ram F downwardly towards the filter member E, with the bubble of air above the liquid discharging upwardly through the bore 48. When liquid starts to discharge from the bore 48 into the cavity 50, the user is assured that the air bubble has been removed from the liquid.

The second protuberance 51 on the plate G is then inserted into the cavity 50, as shown in FIG. 3 to effect a seal therewith. The head 36 of the hypodermic needle D may then be removably mounted on the first protuberance 28.

A user may now force the ram F downwardly relative to the barrel B, with the liquid in the invention A being forced through the filter member E to flow through passages defined by the under surface of filter member E and the grooves 26 to the bore 30. Liquid may discharge from bore 80 to a suitable container (not shown) or flow through the hypodermic needle D when the latter is mounted on first protuberance 28. Solid material that is filtered from the liquid tends to accumulate as a cake on the surface of filter member E most adjacent the first free end 44 on the ram F.

If the material being filtered has a high percentage of solid particled material therein, or material that tends to accumulate as a cake on the filter membrane E-1 such as proteins, to the extent that it seriously impedes the flow of liquid through the filter, the magnetically attractable member M, shown in FIG. 7, is disposed within the confines of the invention A to rest on filter membrane E-1. When the magnetically attractable member M is disposed within the interior of the assembly A, the spacing member 58 is mounted on the first portion 38 of the ram F adjacent the body shoulder 32, as shown in FIG. 7. The spacing member 58 prevents the lower free end 44 of the ram F from contacting the magnetically attractable member M when the latter is disposed on the filter member E (FIG. 7).

After caked solid material accumulates on the upper surface of the filter member E to the extent that it is difficult to force liquid through the filter member E, the hypodermic needle D is removed from the first protuberance 28, and the protuberance inserted into the tapered recess 60 formed in the body K. The body K supports the invention A thereabove, and this body is capable of having the lower surface thereof rest on the upper surface of the table N. The recess 60 is in communication with a horizontal passage 61 that in turn is in communication with a tubular member 63 that extends from the body K. Tubular member 63 is in communication with a hose 65 through which the filtered liquid flows to a suitable conventional container (not shown).

The rotatable magnet 64 is then caused to rotate to create a magnetic field that causes the magnetically attractable member M to move over the upper surface of the filter membrane E-1 to dislodge accumulated solid particled material therefrom, such as proteins.

The invention A may then be removed from the body K, with the hypodermic needle D again being mounted on the first protuberance 28 to permit the filtering of liquid within the confines of the invention A to continue as previously described. The speed of the motor 66, as well as the rate of rotation of the magnet 64, is regulated by a control 92 mounted on the table N, which control is of a conventional nature such as a rheostat, or the like.

The use and operation of the invention has been described previously in detail, and need not be repeated.

I claim:

1. A portable hand-operated device capable of being manipulated by a hand of a user to dispose a quantity of a liquid therein, which quantity of liquid may contain particles of solid material and have an air bubble situated thereabove, and thereafter discharge a desired metered quantity of said liquid free of air and said particles of foreign material therefrom into a desired container or through a hypodermic needle that includes a head in which a tapered recess is defined, said devices including:

a. an elongate cylindrical barrel that has a first end portion on which external threads are defined, and a second end portion that includes an outwardly extending flange that may be engaged by the fore finger and middle finger of said hand;

b. a cup that includes a circular web that has an internally threaded cylindrical side wall extending from the periphery thereof, said web including first and second sides; said first side having a plurality of spaced grooves defined therein; said cup including a tapered first protuberance that extends outwardly from said second side, with said first protuberance having a longitudinal first bore therein that is in communication with said grooves, said first protuberance capable of removably and sealingly engaging said tapered recess in said hypodermic needle head to support said hypodermic needle from said cup, and said internally threaded side wall engaging said external threads to removably support said cup on said barrel;

c. a flat circular filter assembly that includes a screen that rests on said first side and a filter membrane mounted on said screen, said screen and membrane of such diameters as to extend under said first end portion of said barrel, said screen cooperating with said grooves to define a plurality of passages through which said liquid that has been filtered may flow to said first bore;

d. a first resilient sealing ring in said cup that is deformed by pressure contact with the extremity of said first end portion to seal with an outer circumferential portion of said membrane;

e. an elongate ram having first and second longitudinally aligned portions that at their junctions define a circular body shoulder, said first portions of such diameter as to slidably engage the interior of said barrel, said first portion having a first free end surface and said second portion a second free end surface, a longitudinal second bore in said ram that extends between said first end and a cavity that extends inwardly in said ram surface from said second free end surface thereof, said body shoulder acting as a stop when it engages the outer extremity of said second portion of said barrel to prevent said first free end surface of said ram pressure contacting said membrane when said ram is moved inwardly in said barrel, and a circumferential groove in said first portion of said ram adjacent said first free end surface thereof;

f. a second resilient sealing ring mounted in said groove and in slidable sealing contact with the interior of said barrel, with said second longitudinal bore and cavity allowing air from said air bubble to escape to the ambient atmosphere when said ram is moved towards said cup, and the expulsion of all air from said bubble being signaled when liquid from said barrel starts to discharge into said cavity;

g. a plate that may removably overlie said second free end of said ram; and h. first means that project from said plate and removably engage said cavity and seal with the latter after said air from said air bubble has been discharged from liquid in said barrel, with said plate capable of being engaged by the thumb of said hand of said user as said fore finger and middle finger engage said flange to permit said first free end of said ram to be moved towards said cup to force liquid in said barrel through said membrane, with said liquid flowing through said membrane discharging into said passages to flow therefrom into said first longitudinal passage.

2. A device as defined in claim 1 in which said first means includes:

i. a second protuberance that projects from said plate and slidably engages said cavity, said second protuberance having a circumferential groove therein; and j. a third resilient sealing ring mounted in said circumferential groove in said second protuberance that slidably and sealingly engages said cavity.

3. A device as defined in claim 1 which in addition includes:

i. a sequence of graduations and numbers imprinted on said ram, with each of said graduations when aligned with the outer longitudinal extremity of said flange visually indicating to said user the volume of liquid in said barrel.

4. A device as defined in claim 1 which in addition includes:

i. a rigid body having first and second parallel surfaces, a tapered recess that extends inwardly from said first surface that may slidably and sealingly engage said first protuberance to permit said device to be disposed in a vertical position when said second surface rests on a horizontal supporting surface, and a passage in said body in communication with said recess through which liquid that has been filtered may flow to the exterior of said body.

5. A device as defined in claim 4 which in addition includes:

j. an adapter that removably and sealingly engages said cavity when the latter is not engaged by said first means, said adapter capable of being removably and sealingly engaged by the head of a hypodermic needle having a tapered recess therein, with said hypodermic needle capable of being extended through a resilient non-metallic closure on a container for a sterile liquid, and the liquid in said container being withdrawn into said barrel by moving said ram away from said cup to create a negative pressure within said barrel.

6. A device as defined in claim 4 which in addition includes:

j. an elongate magnetically attractable body that rests on said filter member and said magnetically attractable body when moved dislodging said solid particles that have formed a cake on said filter member; and k. magnet means for moving said magnetically attractable body.

7. A device as defined in claim 6 which in addition includes:

l. an envelope of inert material that encases said magnetically attractable body.

8. A device as defined in claim 6 which in addition includes:

l. a ring-shaped member of substantial thickness that extends around said first portion of said ram adjacent said body shoulder, which ring-shaped member acts as a stop by contacting said flange and prevents said first free end of said first portion contacting said magnetically attractable body and forcing the latter into pressure contact with said membrane as said ram is moved towards said cup.

9. A device as defined in claim 6 in which said magnet means includes:

l. a rigid structure having a flat horizontal upper surface on which said body rests;

m. a rotatable magnet within said structure of sufficient strength as to cause said magnetically attractable body to rotate concurrently therewith; and n. third means for rotating said rotatable magnet.

10. A device as defined in claim 1 in which said third means is an electric motor.

* * * * *